United States Patent [19]

Koeda et al.

[11] 4,189,489
[45] Feb. 19, 1980

[54] 5-ALKOXY-PICOLINIC ACID CALCIUM SALTS AND ANTI-HYPERTENSIVE COMPOSITION CONTAINING 5-ALKOXY-PICOLINIC ACID CALCIUM SALTS AND ANTI-HYPERTENSIVE COMPOSITION THEREOF

[75] Inventors: Takemi Koeda, Yokohama; Takashi Tsuruoka, Kawasaki; Uichi Shibata, Tokyo; Hiroyasu Asaoka, Yokohama; Mitsugu Hachisu, Kawasaki; Osamu Itoh; Yasuharu Sekizawa, both of Tokyo; Shigeharu Inouye, Kanagawa; Taro Niida, Yokohama, all of Japan

[73] Assignee: Meiji Seika Kaisha, Ltd., Tokyo, Japan

[21] Appl. No.: 838,180

[22] Filed: Sep. 30, 1977

[30] Foreign Application Priority Data

Sep. 30, 1976 [JP] Japan ................................. 51-116641

[51] Int. Cl.$^2$ .................. A61K 31/445; C07D 213/89
[52] U.S. Cl. ........................................ 424/266; 546/5; 546/269; 546/298
[58] Field of Search .................. 260/295 R, 295.5 R, 260/295 F, 270 E, 297 R; 424/263, 266; 546/298

[56] References Cited

U.S. PATENT DOCUMENTS

| | | | |
|---|---|---|---|
| 3,291,805 | 12/1966 | Ondetti et al. | 260/295 R X |
| 3,519,717 | 7/1970 | Symchowicz et al. | 260/295 R X |
| 3,697,531 | 10/1972 | Lesher | 260/295 AM |
| 3,876,648 | 4/1975 | Haas et al. | 260/295.5 R |
| 3,914,239 | 10/1975 | Kühnis et al. | 260/295 R |
| 4,083,850 | 4/1978 | Koeda et al. | 260/295.5 R |

FOREIGN PATENT DOCUMENTS 2514814 10/1975 Fed. Rep. of Germany ...... 260/295 R

OTHER PUBLICATIONS

Brown et al., Chem. Abst., vol. 80, 1974, parag. 26492p.

*Primary Examiner*—Richard Raymond

*Attorney, Agent, or Firm*—Sughrue, Rothwell, Mion, Zinn and Macpeak

[57] ABSTRACT

5-Alkoxy-picolinic acids and the salts and the esters thereof represented by the formula (I):

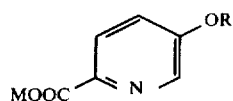

wherein R represents an alkyl group having 1 to 6 carbon atoms and M represents a hydrogen atom; a calcium atom; a sodium atom; a potassium atom; an aluminum atom; an unsubstituted phenyl group; a phenyl group substituted with one or more of an alkyl group having 1 to 4 carbon atoms, an alkoxy group having 1 to 4 carbon atoms or a halogen atom (such as a chlorine, bromine, iodine, etc., atom); a phthalidyl group; an alkoxyalkyl group wherein the alkyl moiety and the alkoxy moiety each has 1 to 4 carbon atoms; or an acyloxyalkyl group having the formula

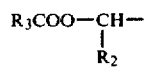

wherein $R_2$ represents a hydrogen atom or a methyl group and $R_3$ represents an alkyl group having 1 to 5 carbon atoms (such as a methyl, n-propyl, isobutyl, t-butyl, etc., group), an alkoxy group having 1 to 4 carbon atoms, a phenyl group, a phenyl group substituted with one or more of an alkyl group having 1 to 4 carbon atoms, an alkoxy group having 1 to 4 carbon atoms or a halogen atom (such as a chlorine, bromine, iodine, etc., atom) or an aralkyl group wherein the alkyl moiety has 1 to 3 carbon atoms, which are useful as anti-hypertensive agents, a process for preparing 5-alkoxy-picolinic acids and the salts and the esters thereof, and anti-hypertensive compositions containing the 5-alkoxy-picolinic acids and the salts and the esters thereof.

6 Claims, No Drawings

5-ALKOXY-PICOLINIC ACID CALCIUM SALTS AND ANTI-HYPERTENSIVE COMPOSITION CONTAINING 5-ALKOXY-PICOLINIC ACID CALCIUM SALTS AND ANTI-HYPERTENSIVE COMPOSITION THEREOF

BACKGROUND OF THE INVENTION

1. Field of the Invention

This invention relates to new and useful compounds, 5-alkoxy-picolinic acids, the pharmaceutically acceptable inorganic salts thereof and the organic esters thereof and to a process for preparing the same.

2. Description of the Prior Art

It has been known that hypertension often induces apoplexy, heart trouble, etc., which necessitates extensive research for new and useful anti-hypertensives.

Fusaric acid (5-n-butylpicolinic acid) is known to be useful as an antihypertensive agent as disclosed in *Jap. J. Pharmocol.*, Vol. 25, 188 (1975), however, fusaric acid has a butyl group at the 5-position of the picolinic acid moiety and has a low $LD_{50}$ value. As a result, an improved antihypertensive agent is desired.

U.S. Patent Application Ser. No. 700,340, filed June 28, 1976, now U.S. Pat. No. 4,083,850 discloses that 3-substituted-2(1H)-pyridone-6-carboxylic acid can be used as an antihypertensive agent but, the antihypertensive activity (i.e., maximum depression in blood pressure) thereof is poor and an improvement is desired.

SUMMARY OF THE INVENTION

As a result of extensive research, it has been found that 5-hydroxy-2-hydroxymethyl pyridine (e.g., as disclosed in *Tetrahedron*, Vol. 20, 2125, (1968)) obtainable easily from nojirimycin (e.g., as disclosed in Japanese Patent Publication 760/1968) provides useful compounds, 5-alkoxy-picolinic acids and pharmaceutically acceptable salts and esters thereof having excellent antihypertensive activity, and have succeeded in providing a new antihypertensive agent.

Accordingly, the present invention, in one embodiment, provides 5-alkoxy-picolinic acids, the inorganic salts thereof and the organic esters thereof represented by the formula (I):

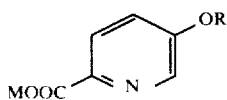

wherein R represents an alkyl group having 1 to 6 carbon atoms and M represents a hydrogen atom; a calcium atom; a sodium atom; a potassium atom; an aluminum atom; an unsubstituted phenyl group; a phenyl group substituted with one or more of an alkyl group having 1 to 4 carbon atoms, an alkoxy group having 1 to 4 carbon atoms or a halogen atom (such as a bromine, chlorine, iodine, etc., atom); a phthalidyl group; an alkoxyalkyl group wherein the alkyl moiety and the alkoxy moiety each has 1 to 4 carbon atoms; or an acyloxyalkyl group having the formula

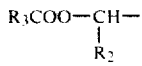

wherein $R_2$ represents a hydrogen atom or a methyl group and $R_1$ represents an alkyl group having 1 to 5 carbon atoms (such as a methyl, n-propyl, isobutyl, t-butyl, etc., group), an alkoxy group having 1 to 4 carbon atoms, a phenyl group, a phenyl group substituted with one or more of an alkyl group having 1 to 4 carbon atoms, an alkoxy group having 1 to 4 carbon atoms or a halogen atom (such as a chlorine, bromine, iodine, etc., atom) or an aralkyl group wherein the alkyl moiety has 1 to 3 carbon atoms.

In a further embodiment, this invention provides a process for preparing a 5-alkoxy-picolinic acid represented by the formula (I'):

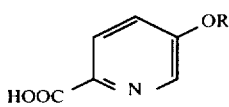

wherein R represents an alkyl group having 1 to 6 carbon atoms, which comprises reacting 5-hydroxy-2-hydroxymethylpyridine of the formula (II):

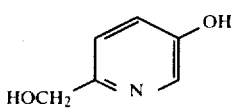

with an alkyl halide of the formula (III):

$$RX \qquad (III)$$

wherein R is as defined above and X represents a halogen atom, to obtain a 5-alkoxy-2-hydroxymethylpyridine of the formula (IV):

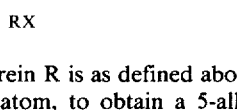

wherein R is as defined above, and oxidizing the 5-alkoxy-2-hydroxymethylpyridine of the formula (IV) with an oxidizing agent.

In a further embodiment of this invention, this invention provides a process for preparing a 5-alkoxy-picolinic acid represented by the formula (I'):

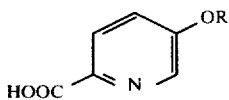

wherein R represents an alkyl group having 2 to 6 carbon atoms, which comprises reacting 5-hydroxy-2-hydroxymethylpyridine of the formula (II):

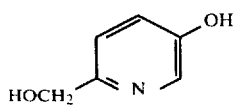

with an alkenyl halide of the formula (III'):

wherein R' represents an alkenyl group having 2 to 6 carbon atoms and X represents a halogen atom, to convert the hydroxyl group at the 5-position of the pyridine nucleus of the 5-hydroxy-2-hydroxymethylpyridine of the formula (II) to an alkenyloxy group thereby producing the corresponding 5-alkenyloxy-2-hydroxymethylpyridine of the formula (IV'):

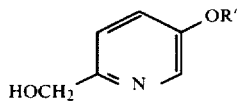

(IV')

wherein R' is as defined above, reducing the alkenyl group of the 5-alkenyloxy-2-hydroxymethylpyridine of the formula (IV') to obtain a 5-alkoxy-2-hydroxymethylpyridine of the formula (IV):

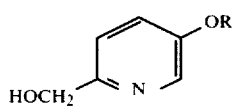

(IV)

wherein R represents an alkyl group having 2 to 6 carbon atoms, and oxidizing the resulting 5-alkoxy-2-hydroxymethylpyridine of the formula (IV) with an oxidizing agent.

In another embodiment of this invention, this invention provides a process for preparing an ester of 5-alkoxy-picolinic acid represented by the formula (I):

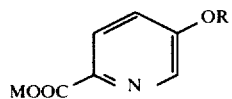

(I)

wherein R represents an alkyl group having 1 to 6 carbon atoms and M represents an alkoxyalkyl group wherein the alkyl moiety and the alkoxy moiety each has 1 to 4 carbon atoms; a phthalidyl group; or an acyloxyalkyl group having the formula

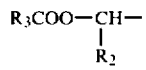

R$_3$COO—CH—
          |
          R$_2$ wherein R$_2$ represents a hydrogen atom or a methyl group and R$_3$ represents an alkyl group having 1 to 5 carbon atoms, an alkoxy group having 1 to 4 carbon atoms, an unsubstituted phenyl groups, a phenyl group substituted with one or more of an alkyl group having 1 to 4 carbon atoms, an alkoxy group having 1 to 4 carbon atoms or a halogen atom or an aralkyl group wherein the alkyl moiety has 1 to 3 carbon atoms, which comprises reacting a 5-alkoxy-picolinic acid or a salt thereof represented by the formula (I''):

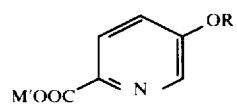

(I'')

wherein R is as described above and M' represents a hydrogen atom, a calcium atom, a sodium atom, a potassium atom or an aluminum atom, with an alkoxyalkyl halide wherein the alkoxy moiety and the alkyl moiety each has 1 to 4 carbon atoms; a 3-bromophthalide; or an acyloxyalkyl halide represented by the formula (V):

(V)

wherein X represents a halogen atom R$_2$ represents a hydrogen atom or a methyl group and R$_4$ represents an alkanoyl group having an alkyl moiety of 1 to 5 carbon atoms, an aroyl group, an alkoxycarbonyl group or an aralkanoyl group, in an organic solvent in the presence of a base.

In even another embodiment of this invention, this invention provides a process for preparing an ester of 5-alkoxy-picolinic acid represented by the formula (I):

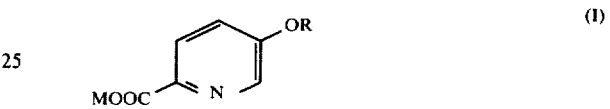

(I)

wherein R represents an alkyl group having 1 to 6 carbon atoms and M represents an unsubstituted phenyl group, a phenyl group substituted with one or more of an alkyl group having 1 to 4 carbon atoms, an alkoxy group having 1 to 4 carbon atoms or halogen atom; which comprises condensing a 5-alkoxy-picolinic acid or a salt thereof represented by the formula (I''):

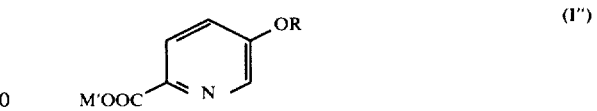

(I'')

wherein R is as described above and M' represents a hydrogen atom, a calcium atom, a sodium atom, a potassium atom or an aluminum atom, with a phenol or a substituted phenol represented by the formula (VI):

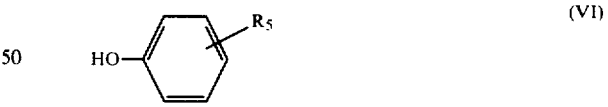

(VI)

wherein R$_5$ represents a hydrogen atom, an alkyl group having 1 to 4 carbon atoms, an alkoxy group having 1 to 4 carbon atoms or a halogen atom, in an organic solvent in the presence of a dehydrating agent.

Also an embodiment of this invention provides a process for preparing an ester of 5-alkoxy-picolinic acid represented by the formula (I):

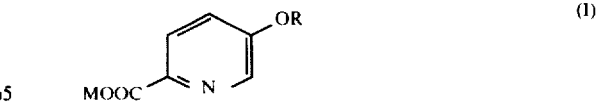

(I)

wherein R represents an alkyl group having 1 to 6 carbon atoms and M represents an acyloxyalkyl group having the formula

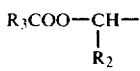

wherein $R_2$ represents a hydrogen atom or a methyl group and $R_3$ represents an alkyl group having 1 to 5 carbon atoms, an alkoxy group having 1 to 4 carbon atoms, an unsubstituted phenyl group, a phenyl group substituted with one or more of an alkyl group having 1 to 4 carbon atoms, an alkoxy group having 1 to 4 carbon atoms or a halogen atom or an aralkyl group wherein the alkyl moiety has 1 to 3 carbon atoms, which comprises reacting a 5-alkoxy-picolinic acid represented by the formula (I'):

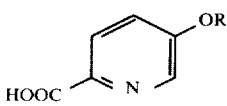

(I')

wherein R represents an alkyl group having 1 to 6 carbon atoms with an acid halogenating agent to produce an acid halide represented by the formula (VII):

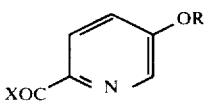

(VII)

wherein R is the same as defined above and X represents a halogen atom,
and further reacting the acid halide of 5-alkoxy-picolinic acid represented by the formula (VII) above with an acyloxyalkanol represented by the formula (VIII):

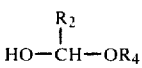

(VIII)

wherein $R_2$ represents a hydrogen atom or a methyl group and $R_4$ represents an alkanoyl group having an alkyl moiety of 1 to 5 carbon atoms, an aroyl group, an alkoxy carbonyl group or an aralkanoyl group, in an organic solvent in the presence of a base.

Also an additional embodiment of this invention provides a process for preparing an ester of 5-alkoxy-picolinic acid represented by the formula (I):

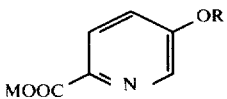

(I)

wherein R represents an alkyl group having 1 to 6 carbon atoms and M represents an unsubstituted phenyl group, an phenyl group substituted with one or more of an alkyl group having 1 to 4 carbon atoms, an alkoxy group having 1 to 4 carbon atoms or a halogen atom: which comprises reacting an acid halide of 5-alkoxy-picolinic acid represented by the formula (VII):

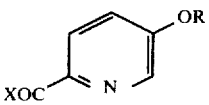

(VII)

wherein R is the same as defined above and X represents a halogen atom,
with a phenol or substituted phenol represented by the formula (VI):

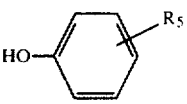

(VI)

wherein $R_5$ represents a hydrogen atom, an alkyl group having 1 to 4 carbon atoms, an alkoxy group having 1 to 4 carbon atoms or a halogen atom, in an organic solvent in the presence of a base.

In an even further embodiment of this invention, this invention provides an antihypertensive composition containing, as an active ingredient, a therapeutically effective amount of at least one 5-alkoxy-picolinic acid or a pharmaceutically acceptable inorganic salt or ester thereof having the formula (I) described above.

DETAILED DESCRIPTION OF THE INVENTION

The term "alkyl group having 1 to 6 carbon atoms" as used herein for R includes straight or branched chain alkyl groups and specific examples include methyl, ethyl, n-propyl, isopropyl, n-butyl, sec-butyl, tert-butyl, n-pentyl, n-hexyl and the like.

Suitable examples of M in the formula (I) include a hydrogen atom; a sodium atom; a calcium atom; a potassium atom; an aluminum atom; an acyloxyalkyl group such as a pivaloyloxymethyl group, an α-pivaloyloxyethyl group, an acetoxymethyl group, an α-acetoxyethyl group, an α-propionyloxyethyl group, a benzoyloxymethyl group, an isobutyryloxymethyl group, an α-(isovaleroyloxy)ethyl group, an α-(benzoyloxy)ethyl group, an α-(p-methoxybenzoyloxy)ethyl group, an α-(3,4,5-trimethoxybenzoyloxy)ethyl group and an α-(ethoxycarbonyloxy)ethyl group; a phthalidyl group; and an alkoxyalkyl group such as a methoxymethyl group and a methoxyethoxymethyl group.

Most preferred examples of M include a hydrogen atom, a calcium atom, a pivaloyloxymethyl group, an α-pivaloyloxyethyl group, an acetoxymethyl group, an isobutyryloxymethyl group, an α-(isovaleroyloxy)ethyl group, an α-benzoyloxyethyl group, an α-(3,4,5-trimethoxybenzoyloxy)ethyl group and a phthalidyl group.

The 5-alkoxy-picolinic acids of the formula (I) above wherein M represents a hydrogen atom and R represents an alkyl group having 1 to 6 carbon atoms can be prepared by reacting 5-hydroxy-2-hydroxymethylpyridine of the formula (II):

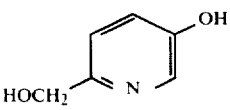

(II)

with an alkyl halide of the formula (III):

RX     (III)

wherein R represents an alkyl group having 1 to 6 carbon atoms and X represents a halogen atom (such as bromine or chlorine), to obtain a 5-alkoxy-2-hydroxymethylpyridine of the formula (IV):

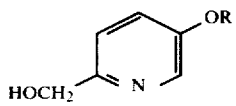

wherein R is as defined above, and oxidizing the resulting 5-alkoxy-2-hydroxymethylpyridine of the formula (IV) with an oxidizing agent or a combination of oxidizing agents.

Alternatively, the compound of the formula (I) above wherein M represents a hydrogen atom and R represents an alkyl group having 2 to 6 carbon atoms can also be prepared by reacting 5-hydroxy-2-hydroxymethylpyridine of the formula (II) above with an alkenyl halide of the formula (III'):

R'X     (III')

wherein R' represents an alkenyl group having 2 to 6 carbon atoms (such as vinyl, allyl, 2-butenyl, 2-pentenyl, 2-hexenyl, etc.) and X represents a halogen atom (such as bromine or chlorine), to convert the hydroxyl group at the 5-position of the pyridine nucleus of the 5-hydroxy-2-hydroxymethylpyridine of the formula (II) into an alkenyloxy group thereby producing a corresponding 5-alkenyloxy-2-hydroxymethylpyridine of the formula (IV'):

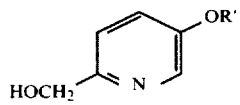

wherein R' is as defined above, reducing the alkenyl group of the 5-alkenyloxy-2-hydroxymethylpyridine of the formula (IV') by hydrogenation to produce a corresponding 5-alkoxy-2-hydroxymethylpyridine of the formula (IV):

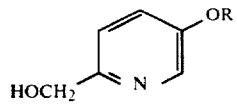

wherein R represents an alkyl group having 2 to 6 carbon atoms, and oxidizing the resulting 5-alkoxy-2-hydroxymethylpyridine of the formula (IV) in the same manner as described above.

This invention also provides an antihypertensive composition containing, as an active ingredient, a therapeutically effective amount of at least one 5-alkoxypicolinic acid of the formula (I) above or a pharmaceutically acceptable inorganic salt or organic ester thereof.

The process for the preparation of the compound of the formula (I) according to this invention is hereinafter described in detail.

In the process of this invention, the 5-hydroxy-2-hydroxymethylpyridine of the formula (II), which can be prepared according to the disclosure in U.S. Pat. No. 2,944,059, can be reacted with an alkyl halide of the formula (III) in an organic solvent such as methanol, ethanol, acetone, dioxane, dimethylformamide, dimethyl sulfoxide, etc., at a temperature of about 20° to about 100° C., preferably 20° to 60° C., for a period of about 3 to about 35 hours, preferably 5 to 20 hours, to obtain a corresponding 5-alkoxy-2-hydroxymethylpyridine.

In the above reaction, the alkyl halide of the formula (III) can be used in an amount of from about 1 to about 5 mols, preferably 1.2 to 1.6 mols, per mol of 5-hydroxy-2-hydroxymethylpyridine of the formula (II).

The reaction between the 5-hydroxy-2-hydroxymethylpyridine of the formula (II) and the alkyl halide of the formula (III) can also be conducted in the presence of a base, e.g., an inorganic base such as sodium hydroxide, potassium hydroxide, sodium carbonate, potassium carbonate, sodium hydrogen carbonate or an organic base such as triethylamine, etc., as a hydrogen halide acceptor, either in water or in an aqueous organic solvent, for example, a mixture of water and an organic solvent as described above, e.g., in an amount of about 10 to about 50% by weight of water.

The base described above can be used in an amount of from about 1 to about 5 mols, preferably 1.2 to 1.6 mols, per mol of the 5-hydroxy-5-hydroxymethylpyridine of the formula (II).

The reaction can be preferably conducted in dimethylformamide or dimethyl sulfoxide since the reaction proceeds most rapidly in such a solvent substantially without producing an N-alkylpyridinium salt as a by-product. In addition, the use of dimethylformamide or dimethyl sulfoxide as a solvent makes it possible to cause a highly selective replacement reaction of the hydroxyl group at the 5-position of the pyridine nucleus, whereby the reaction can be performed easily at a temperature from room temperature (about 15° to about 30° C.) to about 70° C. within a relatively short period of time, e.g., about 3 to about 8 hours. However, the other solvents described above can also be effectively used, although the selectivity of the replacement reaction at the 5-position is somewhat lower than that attainable by the use of dimethylformamide or dimethyl sulfoxide as the solvent. For example, when an alcohol is used as a solvent, a long reaction time is needed such as about 30 hours at 65° C. and, about 30 mol% of an N-alkylpyridinium salt is produced as a by-product.

Alternatively, the intermediate, 5-alkoxy-2-hydroxymethylpyridine, represented by the formula (IV), can also be prepared by reacting 5-hydroxy-2-hydroxymethylpyridine with an alkenyl halide having 2 to 6 carbon atoms of the formula (III') in the same manner as described for the reaction between 5-hydroxy-2-hydroxymethylpyridine and the alkyl halide to obtain an alkenyloxy derivative of the formula (IV'). The alkenyl group of the resulting alkenyloxy derivative is then hydrogenated to produce an alkyl group in the presence of a catalyst such as palladium, platinum oxide, Raney nickel and the like in an organic solvent such as methanol, ethanol or dioxane.

The hydrogenation can be achieved in an atmosphere of hydrogen gas at atmospheric pressure to a pressure of about 5 atmospheres of hydrogen gas, preferably under atmospheric pressure, at a temperature of from about 20° to about 40° C., preferably at room temperature, for a period of about 0.5 to 3 hours, preferably 1 to 2 hours.

The catalyst for hydrogenation described above can be used in an amount of from about 3 to about 20% by weight, preferably 5 to 10%, based on the weight of the alkenyloxy derivative of the formula (IV').

The desired compound of this invention, 5-alkoxypicolinic acid of the formula (I), can be derived from 5-alkoxy-2-hydroxymethylpyridine of the formula (IV) by reacting the latter with an oxidizing agent or a combination thereof such as potassium permanganate, chromic anhydride, potassium dichromate, selenium dioxide, nitric acid and the like in a suitable solvent such as water, sulfuric acid, acetic acid, pyridine, acetone or dioxane.

The oxidation can be achieved using about 1.2 to about 3 mols, preferably 1.5 to 2 mols, of the oxidizing agent per mol of the 5-alkoxy-2-hydroxymethylpyridine of the formula (IV) at a temperature of from about $-10°$ to about $80°$ C., preferably $5°$ to $30°$ C., for a period of from about 1 to about 25 hours, preferably 5 to 10 hours.

In an alternative oxidation procedure, the hydroxymethyl group at the 2-position of the 5-alkoxy-2-hydroxymethylpyridine of the formula (IV) can be first oxidized with a relatively mild oxidizing agent such as active manganese dioxide, e.g., in a molar ratio of about 5:1 to about 20:1 of the manganese dioxide to the compound of the formula (IV), at about $30°$ to about $80°$ C., to convert the hydroxymethyl group into a formyl group and produce a 5-alkoxy-2-formylpyridine compound. A suitable time for this oxidation can range from about 5 to 30 hours. The formyl group of the 5-alkoxy-2-formylpyridine compound is then oxidized into a carboxyl group with silver oxide or hydrogen peroxide at about $40°$ to about $80°$ C. A suitable amount of silver oxide which can be used is a molar ratio of about 1.2:1 to about 2:1 of the silver oxide to the 5-alkoxy-2-formylpyridine compound. A suitable time for this oxidation can range from about 1 to 5 hours.

In the above oxidation, a small amount of certain by-products is occasionally produced, but such by-products can be easily removed using conventional techniques such as solvent extraction, precipitation, crystallization and the like or a combination thereof.

The 5-alkoxy-picolinic acids thus-obtained may be converted into pharmaceutically acceptable inorganic salts such as the calcium, sodium, potassium or aluminum salts using well-known procedures. For example, such a conversion can be advantageously achieved by adding an alkali metal hydroxide, such as sodium hydroxide, potassium hydroxide and the like to a solution or suspension of a 5-alkoxy-picolinic acid of the formula (I) in a solvent such as water at a temperature of about $15°$ C. to about $30°$ C. such that the pH of the solution is about 7. The corresponding calcium and aluminum salts can be prepared from the sodium or potassium salts using calcium and aluminum salts such as calcium acetate monohydrate and aluminum sulfate, respectively.

The 5-alkoxy-picolinic acids of the formula (I) may also be converted into the pharmaceutically acceptable esters such as the pivaloyloxymethyl ester, acetoxymethyl ester, phthalidyl ester, etc., using well-known procedures. For example, such a conversion can be achieved by mixing an acyloxyalkyl halide (such as chloromethyl acetate, chloromethyl pivalate, α-chloroethyl pivalate, α-bromoethyl benzoate, chloromethyl p-methoxy benzoate, bromomethyl butyrate, etc.), an alkoxyalkyl halide or 3-bromophthalide with a 5-alkoxy-picolinic acid of the formula (I), e.g., in a molar proportion of about 1:1.2 to about 1:2 of the 5-alkoxy-picolinic acid to the acyloxyalkyl halide, alkoxyalkyl halide or 3-bromophthalide, in a solvent such as dimethylformamide in the presence of a base, or by condensing a phenol or a substituted phenol and a 5-alkoxy-picolinic acid of the formula (I) using a dehydrating agent (such as dicyclohexylcarbodiimide, etc.). A suitable reaction temperature for the acyloxyalkyl halide, an alkoxyalkyl halide or 3-bromophthalide with 5-alkoxy-picolinic acid ranges from about $-20°$ C. to about $80°$ C., preferably from room temperature (about $15°$ to $30°$ C.) to $50°$ C. and the reaction time is generally about 4 to about 20 hours. A suitable reaction temperature for the phenol or substituted phenol and the 5-alkoxy-picolinic acid ranges from about $0°$ C. to about $40°$ C. and the reaction time generally ranges from about 3 to about 10 hours.

The organic esters of 5-alkoxy-picolinic acids of the formula (I) above wherein R represents an alkyl group having 1 to 6 carbon atoms and M represents an unsubstituted phenyl group; a phenyl group substituted with one or more of an alkyl group having 1 to 4 carbon atoms, an alkoxy group having 1 to 4 carbon atoms or a halogen atom (such as a chlorine, bromine, iodine, etc. atom); a phthalidyl group; an alkoxyalkyl group wherein the alkyl moiety and the alkoxy moiety each has 1 to 4 carbon atoms; or an acyloxyalkyl group having the formula

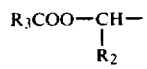

wherein $R_2$ represents a hydrogen atom or a methyl group and $R_3$ represents an alkyl group having 1 to 5 carbon atoms (such as a methyl, n-propyl, isobutyl, t-butyl, etc., group), an alkoxy group having 1 to 4 carbon atoms, a phenyl group, a phenyl group substituted with one or more of an alkyl group having 1 to 4 carbon atoms, an alkoxy group having 1 to 4 carbon atoms or a halogen atom (such as a chlorine, bromine, iodine, etc., atom) or an aralkyl group wherein the alkyl moiety has 1 to 3 carbon atoms, can be prepared, depending on the substituent M, by (a) reacting a 5-alkoxy-picolinic acid or a salt thereof represented by the formula (I"):

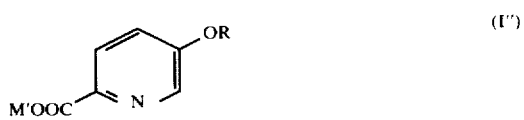

wherein R represents an alkyl group having 1 to 6 carbon atoms and M' represents a hydrogen atom, a calcium atom, a sodium atom, a potassium atom or an aluminum atom, with an alkoxyalkyl halide wherein the alkoxy moiety and the alkyl moiety each has 1 to 4 carbon atoms; a 3-bromophthalide; or an acyloxyalkyl halide represented by the formula (V):

wherein X represents a halogen atom (e.g., as described above), $R_2$ represents a hydrogen atom or a methyl group and $R_4$ represents an alkanoyl group having an alkyl moiety of 1 to 5 carbon atoms, an aroyl group, an alkoxycarbonyl group or an aralkanoyl group in an organic solvent (such as dimethylformamide, dimethyl sulfoxide, etc.) in the presence of a base (such as triethylamine, pyridine, etc.), with a suitable reaction temperature ranging from about −20° C. to about 80° C. and the reaction time generally ranging from about 4 hours to about 20 hours;

(b) condensing a 5-alkoxy-picolinic acid or a salt thereof represented by the formula (I″) above with a phenol or a substituted phenol represented by the formula (VI):

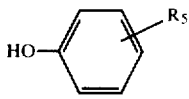

(VI)

wherein $R_5$ represents a hydrogen atom, an alkyl group having 1 to 4 carbon atoms, an alkoxy group having 1 to 4 carbon atoms or a halogen atom (such as chlorine, bromine, iodine, etc.), in an organic solvent (such as chloroform, dioxane, dimethylformamide, pyridine and the like) in the presence of a dehydrating agent (such as dicyclohexylcarbodiimide, etc.), with a suitable reaction temperature ranging from about 0° C. to about 40° C. and the reaction time generally ranging from about 3 to 10 hours;

(c) reacting a 5-alkoxy-picolinic acid represented by the formula (I′):

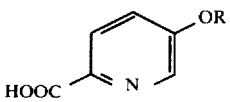

(I′)

wherein R represents an alkyl group having 1 to 6 carbon atoms with an acid halogenating agent (such as phosphorous trichloride, phosphorous tribromide, thionyl chloride, etc.) to produce an acid halide represented by the formula (VII):

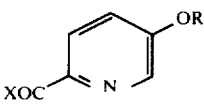

(VII)

wherein R is the same as defined above and X represents a halogen atom (e.g., as described above), and further reacting the acid halide of 5-alkoxy-picolinic acid represented by the formula (VII) above with an acyloxyalkanol represented by the formula (VIII):

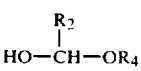

(VIII)

wherein $R_2$ and $R_4$ are the same as defined in the formula (V) above, in an organic solvent (such as benzene, chloroform, methylene chloride, dimethylformamide, dioxane, etc.) in the presence of a base (such as pyridine, triethylamine), with a suitable reaction temperature ranging from about −20° C. to about 50° C. and the reaction time generally ranging from about 1 hour to about 10 hours; or (d) reacting an acid halide of 5-alkoxy-picolinic acid represented by the formula (VII) above with a phenol or substituted phenol represented by the formula (VI) above in an organic solvent (such as chloroform, methylene chloride, dimethylformamide, dioxane, etc.) in the presence of a base (such as pyridine, triethylamine, etc.), with a suitable reaction temperature ranging from about 0° C. to about 40° C. and the reaction time generally ranging from about 3 hours to about 10 hours.

All the compounds of this invention represented by the formula (I) above exhibit a long-lasting antihypertensive activity by oral administration and can be regarded as useful pharmaceutical agents as illustrated in the Example 13 given hereinafter.

It is a known fact that the (hypertensive) activity of antihypertensive drugs is caused more or less by the dilating effect on blood vessels. Therefore, the compounds of the present invention may be used not only as an antihypertensive agent, but as a vasodilator agent, in particular, against peripheral vascular disease.

In general, the compounds of this invention may be administered orally in the form of tablets, capsules or a granular association, with usual pharmaceutical carriers, excipients or diluents. Suitable excipients which can be used include, e.g., calcium phosphate, sodium citrate, glycine, lactose, etc., and additionally binding agents (such as gelatin, gum arabic, polyvinyl pyrrolidone, etc.), lubricants (such as silica, magnesium stearate, etc.), disintegrating agents (such as starch, etc.), wetting agents (such as sodium lauryl sulfate, etc.) can be employed with the compound of this invention in the form of tablets or capsules.

The compound of this invention can be administered orally in the form of an aqueous suspension, an oily suspension, a solution, an emulsion, a syrup and an elixir. Suspending agents (such as methyl cellulose, gelatin, aluminum stearate gel, etc.), emulsifying agents (such as lecithin, sorbitan monooleate, gum arabic, etc.), diluents (such as almond oil, peanut oil, propylene glycol, ethyl alcohol, etc.), preservatives (such as methyl p-hydroxybenzoate, sorbic acid, etc.), sweeteners and flavorings can also be included in the aqueous suspension, oily suspension, solution, emulsion, syrup and elixir.

The compounds of this invention can also be administered in the form of a subcutaneous injection, for example, in the form of a suspension, a solution and an emulsion (e.g., using an oily vehicle or an aqueous vehicle). Usual additives such as suspending agents, stabilizing agents, dispersing agents and preservatives can be included in the suspension, solution and emulsion. The compounds of this invention can also be administered in the form of a suppository containing cocoa butter or glycerides as a carrier.

The calcium salt and the aluminum salt of the compounds of this invention and the esters of the compounds of this invention are not soluble in water and, therefore, they are preferably orally administered, in general. The water-soluble compounds of this invention such as the sodium salt thereof are usually preferably administered non-orally. However, the methods of administration of the compounds of this invention are not limited only to the methods described above.

A suitable dosage amount of the compounds of this invention generally is about 150 mg to about 900 mg per day for an adult and, the compounds of this invention can be administered daily in a single dose or in multiple doses such as two times to four times per day. An appropriate dosage amount is decided according to the age and the body weight of the patient, the condition of the disease and the dose amount and the kind of other medicines which are used together with the compounds of this invention.

The 5-alkoxy-picolinic acid, the pharmaceutically acceptable inorganic salts thereof and the esters thereof can be used as the sole active agent or can be used in combination with one or more other therapeutically active agents. Especially, in hypertension therapy, different antihypertensive agents having different antihypertension activities are usually used in combination. The compounds of this invention can be used in combination with other antihypertensive agents, for example, thiazide-type diuretic antihypertensive agents.

This invention will be illustrated in greater detail by reference to the following Examples, but they are not to be considered as limiting the present invention. Unless otherwise indicated, all percents, parts, ratios and the like are by weight.

EXAMPLE 1

4.48 g of potassium hydroxide was dissolved in a suspension of 10 g of 5-hydroxy-2-hydroxymethylpyridine in 100 ml of water, and the resulting solution was concentrated and dried to obtain the potassium salt of 5-hydroxy-2-hydroxymethylpyridine. The potassium salt thus-obtained was dried in a desiccator and suspended in 200 ml of dimethylformamide. 10.5 g of n-propylbromide was added to the suspension which was then stirred at 60° C. for 8 hours to effect the reaction. The reaction solution was concentrated under reduced pressure, and the resulting dry material was mixed with 200 ml of chloroform and 200 ml of water and two layers formed. The chloroform layer was separated and dried with anhydrous sodium sulfate followed immediately by concentration to obtain 9.8 g of a syrup of 5-n-propyloxy-2-hydroxymethylpyridine. The unreacted materials were found to remain in the aqueous layer. Thin layer chromatography (silica gel) of the thus-obtained product using a solvent system of chloroform-methanol (5:1 by volume) showed a single spot of an $R_f$ of 0.7.

Elemental Analysis for $C_6H_{13}NO_2$: Calculated (%): C 64.67; H 7.78; N 8.38; Found (%): C 64.71; H 7.68; N 8.42

Mass Spectral Analysis: M+ 167

5 g of the above 5-n-propyloxy-2-hydroxymethylpyridine was dissolved in 200 ml of acetone, and 14 g of potassium permanganate was added to the solution over a 2 hour period while stirring the mixture at 40° C. The reaction was further continued for 1 hour at 40° C. and then the reaction solution was immediately concentrated to dryness. 200 ml of a 0.1 N aqueous potassium hydroxide solution was then added to the residue while stirring the mixture, followed by filtration of the mixture. The resulting filtrate was adjusted to a pH of 1.5 with a 5 N aqueous hydrochloric acid solution, and then extracted with 300 ml of chloroform. The chloroform extract was dried with anhydrous sodium sulfate and concentrated to a volume of about 10 ml. 30 ml of ethanol was then added to the concentrate, the mixture was allowed to stand and the product crystallized. The crystals thus-obtained were separated by filtration and dried in a desiccator to obtain 4.2 g of white needle crystals of 5-n-propyloxy-picolinic acid.

Melting Point: 128°–130° C.

Elemental Analysis for $C_9H_{11}NO_3$:
Calculated (%): C 59.67; H 6.08; N 7.73;
Found (%): C 59.70; H 6.18; N 7.67

EXAMPLE 2

5 g of 5-hydroxy-2-hydroxymethylpyridine was suspended in 30 ml of methanol, and 2,16 g of sodium methoxide was added to the suspension. 60 ml of dimethyl sulfoxide was added to the mixture, and the resulting solution was then concentrated to evaporate the methanol. 5.7 g of n-butylbromide was added to the solution in dimethyl sulfoxide and stirred at 50° C. for 6 hours to effect the reaction. After evaporating off the solvent under reduced pressure, the resulting residue was mixed with 150 ml of chloroform and 100 ml of water and two phases separated. The unreacted materials were found to remain in the water layer. The chloroform layer was concentrated to obtain 4.8 g of a syrup of 5-n-butyloxy-2-hydroxymethylpyridine. Thin layer chromatography (silica gel) using a solvent system of chloroform-methanol (5:1 by volume) of the product showed a single spot of an $R_f$ of 0.72.

Elemental Analysis for $C_{10}H_{15}NO_2$: Calculated (%): C 66.30; H 8.29; N 7.73; Found (%): C 66.23; H 8.35; N 7.67

Mass Spectral Analysis: M+ 181

4.5 g of the resulting compound was dissolved in 100 ml of dioxane, and 20 g of activated manganese dioxide was added to the solution followed by stirring the mixture at 60° C. for 14 hours to effect the reaction. The reaction solution was filtered while warm, and the filtrate was decolorized with activated carbon, followed by concentration to obtain 4.3 g of a syrup of 5-n-butyloxypyridine-2-carbaldehyde. Thin layer chromatography (silica gel) of this compound using a solvent system of chloroform-methanol (5:1 by volume) showed a single spot of an $R_f$ of 0.92.

2.9 g of the above compound was then dissolved in 50 ml of methanol, and the resulting solution was added to an aqueous alkaline solution of silver oxide which was prepared from 5 g of silver nitrate and 40 ml of a 2.5 N aqueous sodium hydroxide solution. The resulting mixture was stirred at 60° C. for 2 hours to effect the reaction. The reaction solution was filtered while warm, and the filtrate was washed with 50 ml of a 0.1 N aqueous solution of sodium hydroxide. The combined filtrate and washing was concentrated to about 50 ml, and the concentrate was adjusted to a pH of 1.5 with a 5 N aqueous hydrochloric acid solution followed by extraction with 100 ml of chloroform. The extract was washed with water and dried with anhydrous sodium sulfate, followed by concentration to about 3 ml. 5 ml of ethanol and 6 ml of diethyl ether were added to the concentrate, the mixture was allowed to stand at 3° C. and crystals were obtained. The crystals thus-obtained were filtered to obtain 2.3 g of white needle crystals of 5-n-butyloxy-picolinic acid.

Melting Point: 112°–114° C.

Elemental Analysis for $C_{10}H_{13}NO_3$: Calculated (%): C 61.54; H 6.67; N 7.18; Found (%): C 61.73; H 6.54; N 7.21

EXAMPLE 3

8.85 g of 5-hydroxy-2-hydroxymethylpyridine was suspended in a mixture of 30 ml of water and 300 ml of acetone and 13.5 g of potassium carbonate was added to the suspension followed by stirring at 60° C. for 2 hours while adding dropwise thereto a solution of 10.5 g of allyl bromide in 80 ml of acetone. The reaction solution was further stirred for 2 hours to effect the reaction. The reaction solution was then rendered neutral with a 5 N aqueous hydrochloric acid solution and concentrated, followed by evaporation of any excess of the reagents.

300 ml of ethyl acetate and 200 ml of water were added to the residue and the mixture was then transferred into a separation funnel and stirred thoroughly. An N-allylpyridinium salt produced as a by-product remained in the aqueous layer. The ethyl acetate layer was concentrated to obtain 7.2 g of 5-allyloxy-2-hydroxymethylpyridine.

Elemental Analysis for $C_9H_{11}NO_2$: Calculated (%): C 65.45; H 6.67; N 8.48; Found (%): C 65.38; H 6.70; N 8.42

Mass Spectral Analysis: $M^+$ 165

The above compound was dissolved in 200 ml of ethanol, and the mixture was then subjected to a catalytic reduction with 200 mg of palladium black at room temperature and under atmospheric pressure. The reaction was completed within about 30 minutes. The catalyst was filtered from the reaction mixture and the filtrate was concentrated to dryness, which was then mixed with 300 ml of chloroform and 300 ml of water whereby 2 layers separated. The chloroform layer was concentrated to obtain 6.3 g of a syrup of 5-n-propyloxy-2-hydroxymethylpyridine. 5.0 g of this compound was dissolved in 30 ml of pyridine, to which was further added 9 g of selenium dioxide and the resulting mixture was stirred at 100 to 105° C. for 5 hours to effect the reaction. The selenium precipitated was separated from the reaction mixture by filtration and the filtrate was concentrated to dryness. 100 ml of water was added to the residue and the solution was adjusted to a pH of 9 with a 5 N aqueous sodium hydroxide solution and washed with 50 ml of chloroform. The aqueous layer was separated and adjusted to a pH of 1.5 with a 5 N aqueous hydrochloric acid solution. The mixture was extracted with 100 ml of chloroform, and the chloroform layer separated was decolorized with activated carbon. The chloroform layer was concentrated to about 10 ml, 20 ml of ethanol was added to the concentrate and crystals were obtained. Recrystallization from chloroform-ethanol (1:3 by volume) provided 4.2 g of white needle crystals of 5-n-propyloxy-picolinic acid.

EXAMPLE 4

1.6 g of sodium hydroxide was added to the suspension of 7.3 g of 5-n-propyloxy-picolinic acid in 300 ml water, and the mixture was stirred to obtain an aqueous solution of a sodium salt of the acid. 30 ml of an aqueous solution of 3.6 g of calcium acetate (monohydrate) was added dropwise to the above solution to obtain a precipitate. The resulting precipitate was filtered and washed with water, followed by drying in a desiccator, to obtain 8.1 g of a white powder of the calcium salt of 5-n-propyloxy-picolinic acid.

Melting Point: higher than 230° C.
Elemental Analysis for $C_9H_{10}NO_3 \cdot \frac{1}{2}Ca$
Calculated (%): C 54.00; H 5.00; N 7.00;
Found (%): C 53.81; H 5.16; N 7.02

EXAMPLE 5

975 mg of 5-n-butyloxy-picolinic acid was dissolved in 20 ml of dimethylformamide and, 1.5 g of chloromethylpivalate and 1.4 ml of triethylamine were added to the solution followed by stirring at room temperature for 6 hours. 10 ml of ice-water was added to the reaction solution followed by allowing the mixture to stand for 2 hours and then concentrated. 100 ml of ethyl acetate was added to the resulting residue and the solution was washed with 50 ml each of an acidic aqueous solution (adjusted to a pH of 2 with a 2N aqueous hydrochloric acid solution), an alkaline aqueous solution (adjusted to a pH of 8.5 with a 2 N aqueous sodium hydroxide solution) and water. The ethyl acetate layer was then dried with anhydrous sodium sulfate followed by concentration and then dried under reduced pressure to obtain 1.38 g of an oil of the pivaloyloxymethyl ester of 5-n-butyloxy-picolinic acid. Thin layer chromatography (silica gel) of the thus-obtained product using a solvent system of benzene-acetone (10:1 by volume) showed a single spot of an $R_f$ 0.73.

Elemental Analysis for $C_{16}H_{23}NO_5$:
Calculated (%): C 62.13; H 7.44; N 4.53; Found (%): C 62.18; H 7.38; N 4.48

EXAMPLE 6

975 mg of 5-n-butyloxy-picolinic acid was dissolved in 25 ml of dimethylformamide. 1,010 mg of 3-bromophthalide was added to the solution and then 0.8 ml of triethylamine was further added thereto followed by stirring the mixture at room temperature for 5 hours. 5 ml of ice-water was added to the reaction solution followed by allowing the solution to stand for 2.5 hours. Then the solution was concentrated. 100 ml of ethyl acetate was added to the resulting residue and the solution was washed with 50 ml each of an acidic aqueous solution (adjusted to a pH of 2 with a 2 N aqueous hydrochloric acid solution), an alkaline aqueous solution (adjusted to a pH of 8.5 with a 2N aqueous sodium hydroxide solution) and water. The ethyl acetate layer was then dried with anhydrous sodium sulfate and concentrated to a volume of about 15 ml. The concentrate was allowed to stand at 3° C. to obtain crystals. The crystals thus-obtained were filtered to obtain 1.22 g of crystals of the phthalidyl ester of 5-n-butyloxy-picolinic acid. Thin layer chromatography (silica gel) of the thus-obtained product using a solvent system of benzene-acetone (10:1 by volume) showed a single spot of an $R_f$ of 0.58.

Melting Point: 137°–138° C.
Elemental Analysis for $C_{18}H_{17}NO_5$: Calculated (%): C 66.05; H 5.20; N 4.28; Found (%): C 66.08; H 5.17; N 4.26

EXAMPLE 7

835 mg of 5-n-propyloxy-picolinic acid was dissolved in 25 ml of dimethylformamide and, 850 mg of chloromethyl acetate and 1.3 ml of triethylamine were added to the solution followed by stirring the mixture at room temperature for 4 hours. Precipitated triethylamine hydrochloride was filtered out and the filtrate was concentrated to a volume of about 5 ml. 100 ml of ethyl acetate and 50 ml of water were added to the concentrate and, then, the mixture was adjusted to a pH of 8.5 with a 2 N aqueous sodium hydroxide solution and thereby unreacted compounds and dimethylformamide were transferred to the water layer. The ethyl acetate layer was separated and washed twice with 40 ml of water and dried with anhydrous sodium sulfate. The resulting ethyl acetate solution was concentrated and dried under reduced pressure to obtain 1.14 g of an oil of the acetoxymethyl ester of 5-n-propyloxy-picolinic acid. Thin layer chromatography (silica gel) of the thus-obtained product using a solvent system of benzene-acetone (10:1 by volume) showed a single spot of an $R_f$ of 0.43.

Elemental Analysis for $C_{12}H_{15}NO_5$:
Calculated (%): C 56.92; H 5.93; N 5.53; Found (%): C 57.01; H 5.90; N 5.51

EXAMPLE 8

975 mg of 5-n-butyloxy-picolinic acid was dissolved in 20 ml of dimethylformamide and, 1.52 g of α-pivaloyloxyethyl chloride and 1.4 ml of triethylamine were added to the solution followed by stirring the mixture at room temperature for 20 hours. The same treatment as described in Example 7 above was conducted to obtain an ethyl acetate layer. The obtained ethyl acetate layer was concentrated to obtain a crystalline residue. Recrystallization from hexane gave 1.28 g of crystals of the α-pivaloyloxyethyl ester of 5-n-butyloxy-picolinic acid. Thin layer chromatography (silica gel) of the thus-obtained product using a solvent system of benzene-acetone (10:1 by volume) showed a single spot of an $R_f$ of 0.77.

Melting Point: 67°–68° C.
Elemental Analysis for $C_{17}H_{25}NO_5$:
Calculated (%): C 63.16; H 7.74; N 4.33;
Found (%): C 63.12; H 7.76; N 4.35

EXAMPLE 9

835 mg of 5-n-propyloxy-picolinic acid was dissolved in 20 ml of dimethylformamide and 1.7 g of bromomethylisobutyrate and 1.3 ml of triethylamine were added to the solution followed by stirring at room temperature for 10 hours. 10 ml of ice-water was added to the reaction solution followed by allowing the mixture to stand for 2 hours. Then the mixture was concentrated. 100 ml of ethyl acetate was added to the resulting residue and the solution was washed with 50 ml each of an acidic aqueous solution (adjusted to a pH of 2 with a 2 N aqueous hydrochloric acid solution), an alkaline aqueous solution (adjusted to a pH of 8.5 with a 2N aqueous sodium hydroxide solution) and water. The ethyl acetate layer was then dried with anhydrous sodium sulfate followed by concentration and then dried under reduced pressure to obtain 0.92 g of the isobutyryloxymethyl ester of 5-n-propyloxy-picolinic acid as an oil. Thin layer chromatography (silica gel) of the thus-obtained product using a solvent system of benzene-acetone (10:1 by volume) showed a single spot of an $R_f$ of 0.55.

Elemental Analysis for $C_{15}H_{21}O_5N$: Calculated (%): C 61.02; H 7.12; N 4.76; Found (%): C 61.13; H 7.18; N 4.72

EXAMPLE 10

975 mg of 5-n-butyloxy-picolinic acid was dissolved in 30 ml of dimethylformamide and 1.8 g of α-chloroethylbenzoate and 1.4 ml of triethylamine were added to the solution followed by stirring the mixture at 35° C. for 15 hours. The precipitated triethylamine hydrochloride was filtered out and the filtrate was concentrated to a volume of about 5 ml. 100 ml of ethyl acetate and 50 ml of water were added to the concentrate and, then, the mixture was adjusted to a pH of 8.5 with a 2 N aqueous sodium hydroxide solution and thereby unreacted compounds and dimethylformamide were transferred to the water layer. The ethyl acetate layer was separated and washed twice with 40 ml of water and dried with anhydrous sodium sulfate. The resulting ethyl acetate solution was concentrated and dried under reduced pressure to obtain 1.14 g of the α-benzoyloxyethyl ester of 5-n-butyloxy-picolinic acid as an oil. Thin layer chromatography (silica gel) of the thus-obtained product using a solvent system of benzene-acetone (10:1 by volume) showed a single spot of an $R_f$ of 0.76.

Elemental Analysis for $C_{19}H_{21}O_5N$: Calculated (%): C 66.47; H 6.12; N 4.08; Found (%): C 66.51; H 6.08; N 4.11

EXAMPLE 11

975 mg of 5-n-butyloxypicolinic acid was dissolved in 30 ml of dimethylformamide and 1.65 g of α-(isovaleroyloxy)ethyl chloride and 1.4 ml of triethylamine were added to the solution followed by stirring the mixture at 40° C. for 15 hours. The same treatment as described in Example 5 above was conducted to obtain an ethyl acetate layer. The ethyl acetate layer obtained was concentrated and the residue was dissolved in 5 ml of hexane and allowed to stand at 3° C., and thereby, crystals were precipitated. After filtration, the crystals were dried under reduced pressure to obtain 920 mg of white crystals of the α-(isovaleroyloxy)ethyl ester of 5-n-butyloxypicolinic acid. Thin layer chromatography (silica gel) of the thus-obtained product using a solvent system of benzene-acetone (10:1 by volume) showed a single spot of an $R_f$ of 0.78.

Melting Point: 54–55° C.
Elemental Analysis for $C_{17}H_{25}O_5N$: Calculated (%): C 63.16; H 7.74; N 4.33; Found (%): C 63.08; H 7.79; N 4.29

EXAMPLE 12

975 mg of 5-n-butyloxypicolinic acid was dissolved in 20 ml of dimethylformamide and 2.0 g of α-(3,4,5-trimethoxybenzoyloxy)ethyl chloride and 1.3 ml of triethylamine were added to the solution followed by stirring the mixture at 50° C. for 18 hours. The same treatment as described in Example 7 above was conducted to obtain an ethyl acetate layer. The ethyl acetate layer obtained was concentrated and 2.9 g of the residue was dissolved in 4 ml of benzene. The solution was column chromatographed (silica gel of 100 ml, filled with benzene) and eluted using a solvent mixture of benzene and acetone (30:1 volume ratio) to obtain 10 ml fractions. Fractions 30 to 62 were collected and concentrated and the residue was dissolved in 10 ml of diethyl ether. The solution was allowed to stand at 3° C. and, thereby, crystals were precipitated. After filtration, the crystals were dried under reduced pressure to obtain 2.1 g of crystals of the α-(3,4,5-trimethoxybenzoyloxy)ethyl ester of 5-n-butyloxypicolinic acid. Thin layer chromatography (silica gel) of the thus-obtained product using a solvent system of benzene-acetone (10:1 by volume) showed a single spot of an $R_f$ of 0.61.

Melting Point: 80.0–80.5° C.
Elemental Analysis for $C_{22}H_{27}O_8N$: Calculated (%): C 60.97; H 6.24; N 3.23; Found (%): C 61.02; H 6.21; N 3.18

EXAMPLE 13

Each of the compounds indicated below was suspended in a 1% gum arabic aqueous solution and the suspension was administered orally to groups of spontaneously hypertensive rats (20–25 week-old rats; 5 rats per group; blood pressure before administration: 190–200 mm Hg). These animals are believed to be an experimental model of patients with essential hypertension who occupy about 80% of primary and secondary hypertensions. The change in the blood pressure was then measured by the tail volume method as described in *J. Clin. Invest.*, 18, 373-376 (1936).

The results obtained are shown in the table below.

| Test Compound | Dose (mg/kg) | Maximum Depression in Blood Pressure (%) |
|---|---|---|
| 5-n-Propyloxypicolinic Acid | 100 | 35.7 |
| Calcium Salt of 5-n-Propyloxypicolinic Acid | " | 31.5 |
| 5-n-Butyloxypicolinic Acid | " | 34.3 |
| α-Methyl dopa | " | 17.2 |

In a separate evaluation, each of the compounds to be tested was suspended in a 5% aqueous gum arabic solution containing 2% Tween 80, and the suspension was administered orally to groups of spontaneously hypertensive rats (SHR) (5-20 weeks old; 3 rats per group; blood pressure before administration: 175-190 mm Hg). Arterial blood pressure of concious SHR was recorded from the caudal artery via a pressure transducer (NIHON KOHDEN MP24T) on a polygraph (NIHON KOHDEN RM-85).

The results obtained are shown in the table below.

| Test Compound | Dose (mg/kg) | Maximum Depression in Blood Pressure (%) |
|---|---|---|
| 5-n-Butyloxypicolinic Acid | 100 | 11.2 |
| Pivaloyloxymethyl Ester of 5-n-Butyloxypicolinic Acid | " | 17.5 |
| Acetoxymethyl Ester of 5-n-Propyloxypicolinic Acid | " | 9.8 |
| Isobutyryloxymethyl Ester of 5-n-Butyloxypicolinic Acid | " | 9.5 |
| Fusaric Acid* (control) | " | 10.5 |

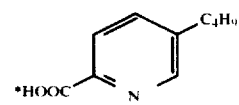

The $LD_{50}$ of the compounds of this invention administered orally in the test rats was also determined and found to be 300-500 mg/kg for the free acids, 800-1,000 mg/kg for the calcium salts, 600-1,000 mg/kg for the acyloxyalkyl esters and the alkoxyalkyl esters and about 1,200 mg/kg for the phthalidyl esters. Fusaric acid, a known antihypertensive agent, showed an oral $LD_{50}$ of 180 mg/kg.

While the invention has been described in detail and with reference to specific embodiments thereof, it will be apparent to one skilled in the art that various changes and modifications can be made therein without departing from the spirit and scope thereof.

What is claimed is:

1. 5-Alkoxy-picolinic acid salts represented by the formula

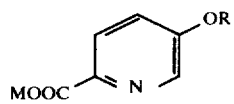

wherein R represents an alkyl group having 1 to 6 carbon atoms and M represents a calcium atom.

2. The 5-alkoxy-picolinic acid salts according to claim 1, wherein R represents an alkyl group having 3 or 4 carbon atoms.

3. 5-n-butyloxy-picolinic acid calcium salt according to claim 1.

4. An antihypertensive composition containing, as an active ingredient, a therapeutically effective amount of at least one 5-alkoxy-picolinic acid salt having the formula

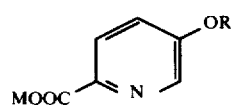

wherein R represents an alkyl group having 1 to 6 carbon atoms and M represents a calcium atom.

5. The anti-hypertensive composition according to claim 4, wherein R represents an alkyl group having 3 or 4 carbon atoms.

6. The anti-hypertensive composition according to claim 4, wherein the 5-alkoxy-picolinic acid salt is 5-n-butyloxy picolinic acid calcium salt.

* * * * *